United States Patent [19]
Haralambopoulos

[11] Patent Number: 5,965,154
[45] Date of Patent: Oct. 12, 1999

[54] ADHESIVE MATRIX TYPE TRANSDERMAL PATCH AND METHOD OF MANUFACTURING SAME

[75] Inventor: Constantine Haralambopoulos, Rochester, N.Y.

[73] Assignee: PLC Holding, L.L.C., Rochester, N.Y.

[21] Appl. No.: 09/042,879

[22] Filed: Mar. 17, 1998

[51] Int. Cl.⁶ .................................................. A61F 13/02
[52] U.S. Cl. ........................ 424/449; 424/447; 424/448
[58] Field of Search ................................. 424/447, 448, 424/449, 487

[56] References Cited

U.S. PATENT DOCUMENTS

| | | | |
|---|---|---|---|
| 5,536,768 | 7/1996 | Kantner et al. | 524/376 |
| 5,593,684 | 1/1997 | Baker et al. | 424/435 |
| 5,626,866 | 5/1997 | Ebert et al. | 424/447 |
| 5,662,991 | 9/1997 | Smolik et al. | 442/319 |

*Primary Examiner*—Thurman K. Page
*Assistant Examiner*—Lakshmi Channavajjala
*Attorney, Agent, or Firm*—Rossi & Associates

[57] ABSTRACT

The invention provides adhesive matrix type transdermal patches and methods for manufacturing the patches. More specifically, the invention utilizes ordinary, prefabricated, commercially available, pressure-sensitive adhesive tapes with skin compatible adhesives, as the structural part of the patch. The adhesive matrix layer of the tape is loaded with the desirable active substances either by embedding, in the case of powders, the active substances in an adhesive matrix layer by the application of heat or pressure, or by a diffusion process for active substances comprising liquids/semi-liquids are carried in located in an embossed release liner or backing layer, which are contact laminated to the adhesive matrix by pressure.

16 Claims, 3 Drawing Sheets

ADHESIVE MATRIX TYPE TRANSDERMAL PATCH AND METHOD OF MANUFACTURING SAME

FIELD OF THE INVENTION

The invention relates to novel adhesive matrix type transdermal delivery patches having an active substance containing pressure sensitive adhesive matrix layer; and to methods for making such a patches by incorporating one or more active substances into the adhesive matrix of ordinary, prefabricated pressure-sensitive adhesive tapes.

BACKGROUND OF THE INVENTION

Transdermal drug delivery is an increasingly important method of drug administration. Transdermal drug delivery patches are similar in appearance to adhesive bandages, and—when attached onto the skin—deliver pharmaceutically and cosmetically active substances (hereinafter referred to as abbreviated as "active substances" and interchangeably used with the term "bioactive substances" and "drug(s)") through the skin. Transdermal drug delivery patches dispense a drug at a controlled rate by presenting the drug for absorption in a efficient manner with a minimum of degradation of the drug, and prevent complications from failure of a patient to comply with a therapeutic regimen. In cosmetic applications, where the desired objective is to deliver effective concentrations of the bioactive substance, such as ascorbic acid, directly to the underlying tissue (the dermal layer) of the skin, transdermal patches have been found to be ideal delivery devices.

Of increasing interest are adhesive matrix type transdermal drug delivery patches in which the bioactive substance is incorporated into a pressure sensitive adhesive layer, which serves not only to carry the bioactive substance but to also attach the patch to the skin. The adhesive matrix type transdermal patch is of simple construction, and is typically comprised of an impermeable backing layer, a single pressure sensitive adhesive, i.e., self-adhesive, layer, the matrix, and a removable protective layer that comprises a release liner. Since the function of such transdermal or dermal (i.e., only topically effective), therapeutic or cosmetic patches and the materials required for their production are well known in the prior art, it will suffice to only mention that one or more bioactive substances are mixed in the pressure sensitive matrix, and that after application of the patch onto the intact skin, the active substances diffuse from the patch into the skin, developing a local or systemic effect.

The adhesive matrix layers are typically manufactured in such a manner that components of the adhesive and their solvents, are mixed with bioactive substances and then coated on a suitable sheet, intended to function as a disposable liner, and the solvents are removed in a drying process. Next, a non-releaseable backing layer is applied over the adhesive matrix layer. The result is a web comprised of a pressure sensitive adhesive matrix layer, containing the bioactive substance(s), sandwiched between a backing layer on one side and a disposable release liner on the other. The web is die cut into suitable sizes and shapes to produce pressure sensitive adhesive transdermal drug delivery patches.

The manufacturing process has serious disadvantages, namely: it is a costly batch-type method which requires a proper mixing of the various ingredients and it is time constrained once the ingredients are mixed together, resulting in a fixed size production runs. Additionally, bioactive substances, as well as the various adjuvants used, may interact adversely with components of the adhesive in the formation reaction of the adhesive. A need therefore exists for methods for making pressure sensitive adhesive matrix type transdermal patches in a economical and continuous process, whereby the bioactive substances do not participate in the formation of the pressure sensitive adhesive matrix layer; and whereby a high concentration of bioactive substances in powder form produces a usable product.

Prior art examples of patches for transdermal delivery of cosmetically active substances include:

U.S. Pat. No. 2,001,862 (Battey; May 1935) discloses adhesive patches in a crescent form or other shapes, medicated with alum for the treatment of wrinkles. The adhesive is dried dextrin, which becomes tacky when wetted with water.

U.S. Pat. No. 3,896,789 (Trancik; July 1975), discloses a pressure sensitive adhesive tape, whose adhesive layer contains a retinoic acid and vitamin E, used for topical treatment of skin diseases.

U.S. Pat. No. 3,949,741 (Hofmann; April 1976), discloses a wrinkle-reducing method whereby pressure sensitive adhesive patches of appropriate shapes are applied to wrinkle-prone areas of the human skin. The adhesive layer of the patch may contain "a small amount of mild acids which promote sloughing off of dead cells on the outer layer of the skin".

U.S. Pat. No. 5,100,672 (Gueret, et al; March 1992) discloses a pressure sensitive adhesive transdermal patch having a composite adhesive layer reinforced with a web layer. Cosmetically bioactive substances used in the patch include water soluble vitamins such as vitamin C, and liposoluble vitamins A and E or their derivatives.

GB 2,265,086 A (Hanet, et al) patent application published on Sep. 22, 1993, discloses the formulation of ascorbic acid and its derivatives, including Sodium Absorbate, into skin whitening pressure sensitive adhesive transdermal patches.

WO 96/14822 patent application (Porter, et al), published on May 23, 1996, discloses a conventionally made adhesive matrix type transdermal patch containing ascorbic acid and some of its derivatives including Sodium Absorbate, for the treatment of wrinkles. The patches are fabricated into crescent and other shapes with rounded corners.

In these references as well, the bioactive substances are mixed with and formulated into a pressure sensitive adhesive matrix which is subsequently coated as a single pressure sensitive adhesive layer, as described earlier.

SUMMARY OF THE INVENTION

The problems of the prior art have been overcome by the present invention, which provides efficient methods for making improved adhesive matrix type transdermal patches. More specifically, the present invention utilizes ordinary, prefabricated, commercially available, pressure-sensitive adhesive tapes, with skin compatible adhesives, as the structural part of the patch. The pressure sensitive adhesive layer of the finished tape is then loaded with the desirable bioactive substances and adjuvants.

It has been found that it is possible to incorporate bioactive substances into the adhesive layer of such prefabricated adhesive tapes, so-called surgical or medical tapes, as well as medical transfer adhesive tapes, whether the bioactive substance is powder, liquid, or semiliquid, e.g., a gel or an emulsion by arranging a thin layer of the bioactive substance between the adhesive surface of a tape and its release liner (or its backing layer, for a transfer tape), and subjecting the assembly to moderate heat and/or pressure so as to laminate the assembly. As a result, the bioactive substance becomes incorporated into the adhesive matrix of the tape—either by mechanical embedding, for powders or by a diffusion process for liquids—while the tape remains adhesive over its entire delivery surface, i.e., the surface that comes in contact with the skin. Patches of suitable size and shape fabricated from the tape, function as an adhesive matrix type transdermal pressure sensitive adhesive patches when attached to intact skin.

In one embodiment a transdermal patch comprises a pressure sensitive adhesive tape (either as a continuous web or a segment) including a backing layer and a pressure sensitive adhesive matrix; an active layer including at least one active substance embedded in the adhesive matrix; and a release liner located on the adhesive matrix. The active layer can be either uniform and continuous, discontinuous or embedded in the adhesive matrix such that a margin of the adhesive matrix is formed around the active layer.

A process for manufacturing such a transdermal patch includes the steps of depositing an active layer including at least one active substance on an adhesive side of a pressure sensitive adhesive tape, applying at least one of heat and pressure to the adhesive matrix to drive the active substance into the adhesive matrix; and locating a release liner on the adhesive matrix.

In a another embodiment, a transdermal patch comprises an adhesive transfer tape including a release liner and an adhesive matrix; at least one active substance, formed as at least one of a random discontinuous pattern and an ordered discontinuous pattern, that is embedded in the adhesive matrix; and a backing layer located on the adhesive matrix.

The transdermal patch is manufactured by depositing at least one active substance on an adhesive layer of an adhesive transfer tape in at least one of a random discontinuous pattern and an ordered discontinuous pattern, locating a backing layer on the adhesive matrix; and laminating the backing layer to the transfer adhesive tape by the application of pressure.

In a further embodiment, a transdermal patch is provided comprising an adhesive tape including a first adhesive matrix formed on a backing layer; an adhesive transfer tape including a second adhesive matrix formed on a release liner; and at least one active substance located between said first adhesive matrix and said second adhesive matrix.

The transdermal patch is manufactured by depositing a layer of active substance on an adhesive matrix of a first adhesive tape; locating a second adhesive tape on the layer such that an adhesive matrix of the second adhesive tape contacts the layer and laminating the first adhesive tape, the layer and the second adhesive tape together by the application of pressure. The first adhesive tape comprises a backing layer having one side coated with the adhesive matrix of the first adhesive tape and the second adhesive tape comprises a release layer located on the adhesive matrix of the second adhesive tape. Alternatively, the first adhesive tape comprises a release layer located on the adhesive matrix of the first adhesive tape and the second adhesive tape comprises a backing layer formed on the adhesive matrix of the second adhesive tape.

In a still further embodiment, a transdermal patch is provided that comprises an embossed release liner including a plurality of depressions, at least one active substance comprising at least one of a liquid and semi-liquid deposited in the depressions; and an adhesive tape comprising an adhesive matrix applied to the embossed release liner and a backing layer located on the adhesive matrix. The embossed release liner is comprised of a material that will not permanently attach to the adhesive tape after lamination.

The transdermal patch is manufactured by depositing an active substance comprising at least one of a liquid and a semi-liquid in depressions of an embossed release liner; locating an adhesive tape including an adhesive matrix and a backing layer over the embossed layer, wherein the adhesive matrix is in contact with the embossed liner; and laminating the embossed liner to the pressure sensitive adhesive tape.

In another embodiment, a transdermal patch is provided comprising an embossed backing including a plurality of depressions; at least one active substance comprising at least one of a liquid and semi-liquid deposited in the depressions; and an adhesive transfer tape comprising an adhesive matrix applied to the embossed backing a transfer layer located on the adhesive matrix.

The transdermal patch is manufactured by depositing an active substance comprising at least one of a liquid and a semi-liquid in depressions of an embossed liner; locating an adhesive transfer tape including an adhesive matrix and a transfer layer over the embossed layer, wherein the adhesive matrix is in contact with the embossed backing; and laminating the embossed backing to the pressure sensitive adhesive transfer tape.

BRIEF DESCRIPTION OF THE DRAWINGS

The invention will be described with greater reference to the following detailed description of the preferred embodiments and the accompanying drawings, wherein.

DETAILED DESCRIPTION OF THE PREFERRED EMBODIMENTS

The present invention eliminates the difficulties and disadvantages associated with the prior art transdermal patches, by providing methods for making novel pressure sensitive adhesive matrix type transdermal patches, whereby pharmaceutically or cosmetically active substances are incorporated into the adhesive matrix of ordinary prefabricated pressure sensitive adhesive tapes by a momentary application of relatively low heat and/or pressure in a lamination-like operation. Such transdermal patches can be readily and economically produced in a continuous process, from ordinary, prefabricated, commercially available, inexpensive medical tapes, widely used in hospitals and doctors' offices for securing wound dressings. The present invention may also be carried out by using prefabricated medical adhesive transfer tapes, which are comprised of a pressure sensitive adhesive layer sandwiched between two release liners, of two different degrees of adhesion to the matrix. To use, the more weakly adhered liner is first removed and the exposed adhesive layer is contacted with the surface (e.g., skin), to be transferred on, and the second protective liner is the peeled off, leaving a pure pressure sensitive adhesive layer on the surface. Conveniently, adhesive transfer tapes also come in rolls with only one release liner, non-stick on both sides.

A variety of adhesives may be used in the manufacture of such pressure sensitive adhesive tapes, for example, acrylic and methacrylic ester homo-or copolymers, butyl rubber based systems, silicones, urethanes, vinyl esters and amides, olefin copolymer materials, natural or synthetic rubbers, and the like, including hot-melt adhesives (See, for example, U.S. Pat. No. 5,387,450).

Examples of materials suitable for the use as backing layers of such pressure sensitive adhesive tapes include films of polyethylene, polyethylene terepthalate, polypropylene, polyurethane, ethylene vinyl acetate of polyamide. Metal foils, e.g. aluminum foil or paper, alone or coated with a polymeric material, may also be used.

The release liner is the removable protective sheet of plastic or paper that has been rendered "non-stick" to the pressure sensitive adhesive. Release liners are known in the art and are disclosed for example in U.S. Pat. No. 4,386,135.

Two typical prefabricated medical tapes, commercially produced by 3M Company, St. Paul, Minn. are:
 a) No. 1525-L which has an occlusive backing of polyethylene film of 3 mil thickness a 1.4 mil thick hypoallergenic, pressure sensitive acrylate adhesive layer and comes with a paper release liner coated with polyethylene and silicone; and
 b) No. 1524 medical transfer adhesive tape, which is 2.5 mil thick, hyporallergenic, pressure sensitive acrylate adhesive, containing polyester fibers, and the liner is paper silicone coated on both sides. The tapes are manufactured in large rolls ("log rolls"), in widths up to 48 inches and several hundred yards long.

Figure 1:
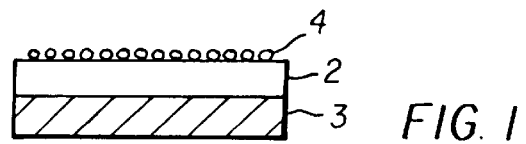
FIG. 1. shows a cross section of a patch of a prefabricated, pressure sensitive adhesive tape having a thin layer of a powdered bioactive substance covering the exposed surface of the adhesive matrix according to the first embodiment of the present invention.

A first embodiment of the invention will be described with reference to FIGS. 1–3. In the first embodiment, an active substance (or mixture of substances) in powder form is sprinkled or otherwise deposited or spread uniformly as a thin layer 4 on an exposed adhesive surface of a patch of a prefabricated pressure sensitive adhesive tape, which is comprised of a backing layer 3 and a pressure sensitive adhesive matrix 2 as shown in FIG. 1. The thin layer 4 on the adhesive surface may be uniform and continuous without leaving any areas of the adhesive matrix 2 uncovered; or it may be random and discontinuous, wherein the powder particles are randomly distributed over the adhesive surface but leave elemental inter-particle areas of the adhesive matrix 2 uncovered. A random and discontinuous layer may be formed, for example, by sprinkling the powder through a sieve over a traveling web of the adhesive tape. The powder layer may also be deposited in an ordered discontinuous pattern, i.e., a discontinuous, regular pattern of discrete powdered areas—such as lines or dots in a screen or halftone-like arrangements—surrounded by uncovered areas of the adhesive matrix 2. An ordered discontinuous pattern, for example, may be formed by depositing a powder contained on a cylinder whose circular wall is made of a perforate screen, while the cylinder contacts a traveling pressure sensitive adhesive tape and it turns with the same linear velocity as that of the tape. Lastly, the thin layer 4 may be a uniform and continuous monolayer which is a contiguous layer of single powder particles without leaving any areas of the adhesive matrix 2 uncovered. A powder monolayer may be formed, for example, by passing a pressure sensitive adhesive tape through a quantity of a powder and then the shaking off excess powder or removing it by lightly vacuuming the powered adhesive matrix 2 without physically contacting the powdered surface. The thin layer 4 of powder that remains on the tape is comprised of contiguous powder particles that cling superficially to the adhesive matrix 2.

Figure 2:
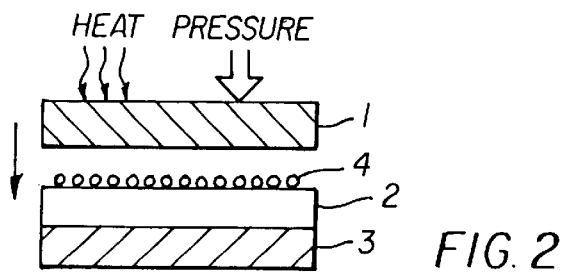
FIG. 2. shows in cross section a release liner in overlaying contact with the powdered surface of the patch of FIG. 1, and schematically illustrates the simultaneous application of heat and pressure, so as to laminate the assembly, according to the first embodiment of the present invention.
Figure 3:
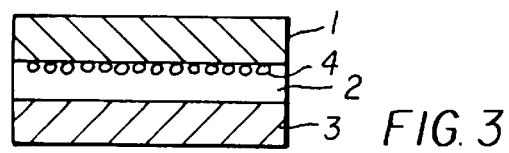
FIG. 3. shows a cross section of the finished transdermal adhesive matrix type patch, with the powder layer incorporated into the adhesive matrix, just beneath its surface, according to the first embodiment of the present invention.

A release liner 1 is brought in overlaying contact with the thin layer 4 as shown in FIG. 2, and the assembly is subjected momentarily to relatively low heat and pressure, for example by rollers, to laminate the various layers together as a completed patch as shown in FIG. 3. During this process, the thin layer 4 is effectively driven into the adhesive matrix 2, where it becomes embedded at a depth just below the surface of the adhesive matrix 2, as evidenced by the fact that the entire surface area of the adhesive matrix 2, previously powdered and non-tacky, regains its pressure sensitive adhesive properties. The laminated layers are then cut to length to form a patch assembly. The resulting patch assembly is not permanently laminated together, as the release liner 1 can be easily peeled off prior to use, because the release liner 1 in contact with the adhesive matrix 2 is either made of a non-stick material or the surface of the release liner is coated with a non-stick material.

The mechanism of the absorption of the powdered thin layer 4 by the adhesive matrix 2 is that, as the adhesive is heated to a temperature at or within its glass transition temperature (Tg) range, it becomes progressively plasticized, i.e., less viscous, to flow around and engulf the powder particles in contact with the adhesive, thus incorporating the powder into the adhesive matrix. After cooling at room temperature, the powder particles end up embedded in the "re-solidified" (i.e., its return to its initial viscosity), adhesive matrix. The simultaneous application of pressure assures the intimate contact of the powder layer with the heat-plasticized adhesive, and as soon as an optimum plasticity is reached, the powder, is promptly "sunk" or "driven" into adhesive matrix. The process may be viewed as the equivalent of loading the (empty) matrix of a pressure sensitive adhesive tape with a quantity of a bioactive substance in powder form, by heating the adhesive to a sufficient plasticity (i.e. softness), via a lamination processing step, hence the term Intra-Matrix Powder Lamination (IMPL), which will be used hereinafter as being descriptive of the process and the effect.

The range of temperatures required to effect IMPL depends on the Tg of a particular adhesive polymer system. At a minimum IMPL temperature, the adhesive merely softens to sufficient plasticity for the powder to be incorporated into the adhesive matrix. In general, the minimum temperature falls in the lower end of a Tg. Tapes having a relatively low Tg are preferable because various substances may be incorporated in the tapes using the IMPL method, without the danger of heat damage. Pertinent experiments with the acrylate tapes on hand indicate that temperatures between 150° F. and 285° F. (65.5° C.–140.5° C.), constitute and optimum working range of temperatures for the IMPL process.

The corresponding minimum value in the range of IMPL pressures is the pressure sufficient to maintain the powder and the softened adhesive in intimate contact. In general the higher the IMPL temperature allowable, the lower the required pressure. With the acrylate adhesive tapes described above, the minimum IMPL pressure can be as low as ½ lb./square inch.

Experiments with powdered ascorbic acid and commercially available medical tapes with acrylate-type pressure sensitive adhesive, have shown that the amount of powder that is incorporated into a transdermal patch, by the IMPL process is the single most important consideration in the design of the patch in determining the final adhesion characteristics of the patch. An empirical formula has been derived that gives the amount Wp of the powder incorporated in the adhesive in terms of the weight Wa of the adhesive matrix in which it is contained, the average particle size P of the powder and the thickness h of the adhesive layer of the prefabricated tape, namely:

$$Wp = Wa((a-b)P/h) \qquad \text{Eq. (1)}$$

where Wp and Wa are in mg/square inch.

The factors a and b are numerical constants whose values are experimentally determined and which depend on the particular powder substance employed—whether it is absorbing, non-absorbing, amorphous or crystalline and its specific crystalline form. For powdered ascorbic acid, for example, which comes in crystals, usually plates, sometimes needles of the monoclinic crystalline form the numerical constants were found to be a=0.50 and b=0.10. Substituting these values in equation (1), it becomes specific for ascorbic acid, or:

$$Wp = Wa(0.5-(0.1)P/h) \qquad \text{Eq. (2)}$$

It must be noted that equations (1) and (2) give the maximum allowable weight of a powder that can be incorporated in the adhesive matrix by the IMPL process, yielding a patch having approximately ½ the adhesion of the intact prefabricated tape.

As an example, for the ultra fine powder of ascorbic acid (manufactured by Hoffman La Roche, Paramus, N.J.), specified with an average particle size P=44 microns, (corresponding to US sieve number 325), and for medical tape No. 1525-L having the nominal specifications, as supplied by its manufacturer, h=36 microns (corresponding to 1.4 mil) and Wa=20 mg/sq.inch.(i.e., the dry coating weight of the adhesive), equation (2) yields: Wp=20 (0.5–(0.1)44/36) mg./sq. inch or Wp=7.5 mg/sq. inch, meaning that for parameters specified, 7.5 mg./sq. inch of ascorbic acid is the maximum powder loading attainable by the IMPL process, resulting in a patch having ½ of the adhesion of the prefabricated tape.

The weight percent loading WL in the above example is then (by definition):

$$WL = (7.5 \text{ mg}/(20 \text{ mg} + 7.5 \text{ mg})) \times 100 \text{ or } WL = 27\%.$$

The theoretical maximum loading limit tends to the value:

$$WL = (a/(a+1)) \times 100$$

(derived from Eq. (1) for P/h=0), or (WL)max=(0.5/(0.5+1))×100, or WL (max)=33%

On the other hand, for Wp=0 or 0.5–(0.1)P/h=0, then P/h=5, meaning that for the above specified example for P/h>5 the IMPL process yields an unusable, non-adhesive patch. It is therefore preferably that the ratio P/h be equal to or less than five.

It was found that a powder loading of around 7.5 mg./sq. inch of ultra fine ascorbic acid corresponds to the powder monolayer, which forms easily and reproducibly by applying the ultra fine powder on the adhesive side of the tape and removing the excess powder as by lightly vacuuming the powdered surface without physically contacting the powdered surface. The same powdering process yields around 15 mg./sq. inch of fine powder ascorbic acid having an average particle size of 150 microns (or US sieve number 100), which requires a tape having a thicker adhesive.

Testing various values for h in Eq. (2), and considering that Wa/h=20 mg/sq.inch/36 microns it is found that for h=85 microns and a corresponding Wa=47 mg./sq.inch, Eq. (2) yields: Wp=47 (0.5–(0.1)150/85) mg./sq. inch or Wp=15.2 mg./sq. inch, meaning that a prefabricated tape of thickness at least 85 microns (approximates to U.S. sieve number 170) and having a dry coating weight of 47 mg./sq. inch is required to incorporate fine ascorbic acid powder in a tape via the IMPL process. In applications involving a mixture of powdered substances having different particle sizes, the calculations using Eq. (1) are based on the highest P/h ratio for a given power-tape system.

The capacity of a patch to carry a powdered active substance can be increased by increasing the thickness of the medical tapes matrix in one or more increments. The matrix increments come from a prefabricated adhesive transfer tape (such as the previously mentioned No. 1524), whereby the transfer tape is laminated by pressure only ("cold" lamination) to the adhesive surface of the medical tape. In this way, a prefabricated pressure sensitive adhesive tape of a given matrix thickness can be built up to any desired thickness by repeating the adhesive transfer process as described.

Figure 4:
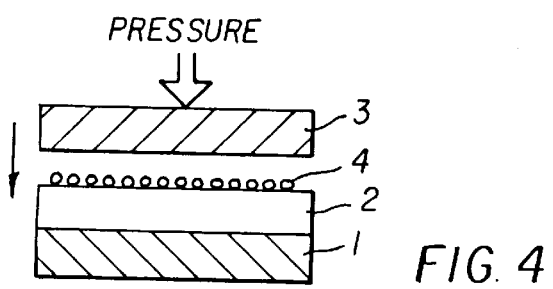
FIG. 4. shows a cross section of a patch of a prefabricated transfer pressure sensitive adhesive tape on liner, having a thin layer of a powdered active substance, covering the exposed surface of the adhesive matrix, in a screen-like pattern; and a backing layer in overlaying contact with the powdered surface, while schematically illustrating the application of pressure only, whereby to laminate ("cold lamination") together the assembly, according to a second embodiment of the present invention.
Figure 5:
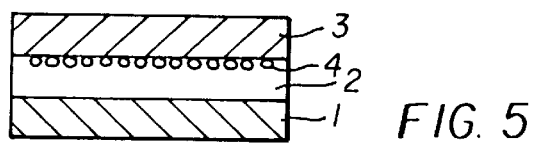
FIG. 5. shows a cross section of the finished adhesive matrix type patch with the patterned powder layer interlaminated in the backing/adhesive interface, according to the second embodiment of the present invention.

Applicant has also found that powdered substances may be incorporated in a transdermal patch inter-laminarly, i.e., between the backing and the adhesive pressure sensitive adhesive layer of a medical adhesive tape, without the application of heat. The process is referred to as Powder Inter Lamination (PIL). By the PIL process (constituting a second embodiment of the invention), the powder 4 is deposited as a discontinuous layer on an adhesive transfer tape that includes an adhesive matrix 2 formed on a release liner as shown in FIG. 4. The powder pattern is then overlaid with a backing layer 3 (such as polyethylene) and the assembly is subjected to pressure only, so as to laminate the assembly together. The applied pressure forces the adhesive through the areas that are not covered by powder, to contact the backing layer and instantly bond to it in these areas, thus trapping and securing the layer of the discontinuous powder pattern between the backing of the patch and the pressure sensitive adhesive matrix, as shown in FIG. 5.

The PIL process has two distinct advantages:
(1) it can be carried out at room temperature or even lower temperatures, to accommodate temperature-sensitive substances, and
(2) the adhesion of the delivery side of the patch (i.e., the skin contacting surface), remains unchanged, i.e., the same as that of the initial tape.

Figure 6:
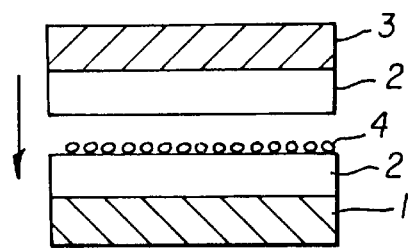
FIG. 6. shows a cross section of a patch of a prefabricated transfer pressure sensitive adhesive tape having monolayer of powder particles covering its exposed surface; and a pressure sensitive adhesive tape in overlaying facing contact with the powdered surface, while schematically illustrating the application of pressure only to laminate ("cold lamination") the assembly together according to a third embodiment of the present invention.
Figure 7:
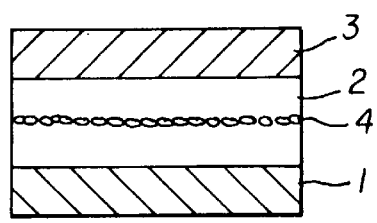
FIG. 7. shows a cross section of the finished adhesive matrix type transdermal patch of FIG. 6, with the powder monolayer interlaminated between the two adhesive matrices, according to the third embodiment of the present invention.

In a third embodiment of the invention, a continuous monolayer powder layer 4 shown in FIGS. 6 and 7, is laminated by pressure only, in the interface of two adhesive matrices: one of a pressure sensitive adhesive tape, and the other of an adhesive transfer tape. This particular process is referred to as Matrix-to-Matrix Powder Lamination (MMPL), and it has been found to be independent of a powder's particle size (which is the principal advantage of the process). The MMPL process is also applicable with discontinuous type power layers as in the PIL process described above.

It must be noted that PIL and MMPL processes are particularly suitable for powders comprised of microcapsules, containing one or more bioactive compositions, as the pressure applied for lamination in minimal and therefore, the danger of rupturing the microcapsules is all but eliminated.

It has been also been found that the bioactive liquid substances, or semiliquids, such as gels and emulsions, can also be incorporated in the adhesive matrix of plain prefabricated pressure sensitive adhesive tapes by depositing a measured quantity of the liquid/semi-liquid on a release liner sheet, which is embossed (either pre-embossed or embossed as part of a continuous manufacturing process to form the transdermal patch) with a multitude of small depressions or pits and laminating the release liner to the adhesive matrix of the tape by pressure only. As a result, the liquid/semi-liquid substance is incorporated into the adhesive matrix by diffusion. The process is referred to as Inter-Laminar Matrix Diffusion (ILMD).

Figure 8:
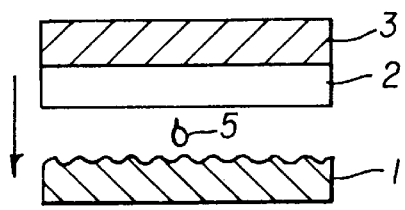
FIG. 8. shows a cross section of a patch of a prefabricated pressure sensitive adhesive tape in overlaying contact with a release liner which is embossed with a plurality of indentations and which contain a measured amount of an active substance in liquid or semi-liquid state, schematically illustrated as a drop, while schematically illustrating the application of pressure only preparatory to "cold lamination" of the assembly according to a fourth embodiment of the present invention.
Figure 9:
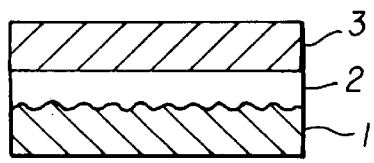
FIG. 9. shows a cross section of the finished adhesive matrix type transdermal patch, in the adhesive matrix of which the entire quantity of liquid/semiliquid of FIG. 8 has diffused, according to the fourth embodiment of the present invention.

FIGS. 8 and 9 illustrate the ILMD process. A requisite, measured, quantity of liquid or semi-liquid (gel or emulsion), of a bioactive substance, schematically shown in FIG. 8 as a liquid drop 5, is deposited on the surface of a release liner 1. The liner surface has a multitude of fine (meaning small) depressions or pits, produced for example by mechanically embossing the liner in any random or patterned arrangement, so that the total volume of the depressions/pits over the patch area is at least equal or greater to the volume of the applied liquid/semi-liquid. Next, a pressure sensitive adhesive tape is overlaid on the embossed liner and pressure is applied to the assembly as to laminate it together. The resulting assembly (patch) has only superficially laminated the embossed liner, as the liner surface in contact with the pressure sensitive adhesive is non-stick (siliconized).

It should be noted that it is not necessary for the liquid/ semi-liquid to be evenly spread over the entire liner surface before lamination (cold), because the liquid/semi-liquid substance distributes itself in the pits/depressions of the embossed liner upon being "squeezed" between tape and liner. This feature of embossed liner distinguishes the fourth embodiment from the prior art including that shown in U.S. Pat. Nos. 5,626,866; 5,569.484, 5,110,599, and 4,915,950. Additionally, this embodiment uses only a single pressure sensitive adhesive matrix, to produce an adhesive matrix type transdermal patch. Furthermore, there is no example in the prior art of an adhesive matrix type transdermal patch having an embossed liner as a functional part of the patch.

Figure 10:
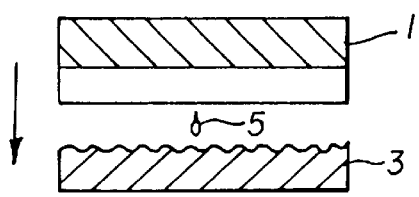
FIG. 10, as in FIG. 9, with the exception that an adhesive transfer tape is used, instead of a pressure sensitive adhesive tape, according to the fifth embodiment of the present invention.
Figure 11:
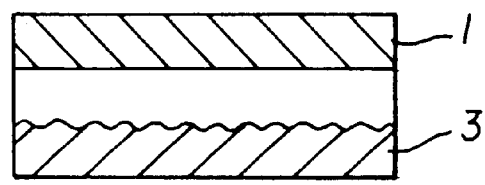
FIG. 11. shows a cross section of the finished adhesive matrix type transdermal patch of FIG. 10, according to the fifth embodiment of the present invention.

FIGS. 10 and 11 illustrate the ILMD process as described, utilizing an adhesive transfer tape instead of a pressure sensitive adhesive tape. In this embodiment, the backing layer is embossed with pits and depressions.

Figure 12:
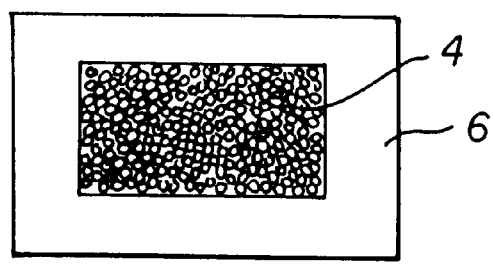
FIG. 12. shows a top view of a patch of a prefabricated pressure sensitive adhesive tape whose central portion only has a powder embedded therein according to a sixth embodiment of the present invention, FIG. 13. shows a cross section of the patch of FIG. 12 in which the powder is embedded as a continuous layer.
Figure 13:
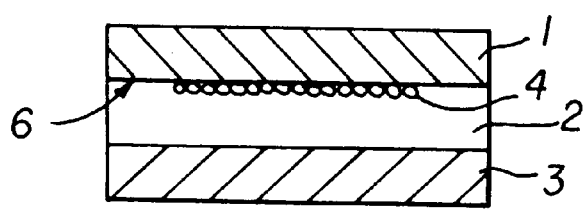
Figure 14:
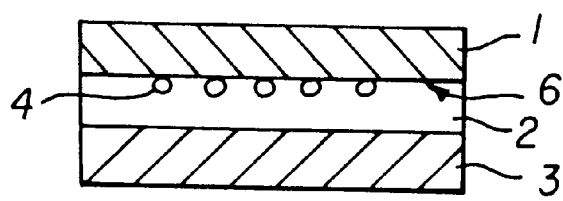
FIG. 14. shows a cross section of the patch of FIG. 12 in which the powder is embedded as a discontinuous layer.

FIG. 12 illustrates yet another embodiment (sixth embodiment) of an adhesive matrix type transdermal patch according to the present invention, wherein a bioactive powdered substance 4 is embedded (by the IMPL process) in the central area. The adhesive margin ensures secure adhesion of the patch to the skin. The process is referred to as Margined IMPL process (M-IMPL). FIG. 13 shows a cross section of the M-IMPL patch of FIG. 12 formed from a continuous powder layer; whereas FIG. 14 shows a cross-section of the M-IMPL patch of FIG. 12 formed from a discontinuous powder layer. A powdered substance may be deposited in the general pattern of FIG. 12 by the use of a mechanical "mask" having a central opening, which is placed over the adhesive surface of a tape, producing a continuous type powder layer. The powder is distributed in a discontinuous layer by substituting the central mask opening with a screen.

Adhesive matrix type transdermal patches of the present invention can be used for the application of virtually any pharmaceutical substance and any cosmetic substance (including substances capable of improving the appearance and or feel of the skin) that are suitable for topical administration.

The invention has been described with reference to certain preferred embodiments thereof it will be understood, however, that modifications and variations are possible within the scope of the appended claims.

What is claimed is:

1. A transdermal patch made by the process of:

depositing an active layer of at least one active substance on an adhesive matrix located on a backing layer of a pressure sensitive adhesive tape, wherein said at least one active substance comprises at least one of a powder, a liquid and a gel;

bringing a release liner into contact with the adhesive matrix; and applying pressure to the adhesive matrix to drive the active substance into the adhesive matrix.

2. A transdermal patch as claimed in claim 1, wherein the active layer is uniform and continuous.

3. A transdermal patch as claimed in claim 1, wherein the active layer is discontinuous.

4. A transdermal patch as claimed in claim 1, wherein the active layer is embedded in the adhesive matrix such that a margin of the adhesive matrix is formed around the active layer.

5. A process for manufacturing a transdermal patch comprising the steps of:

depositing an active layer of at least one active substance on an adhesive matrix located on a backing layer of a pressure sensitive adhesive tape, wherein said at least one active substance comprises at least one of a powder, a liquid and a gel;

bringing a release liner into contact with the adhesive matrix; and applying pressure to the adhesive matrix to drive the active substance into the adhesive matrix.

6. A transdermal patch as claimed in claim 5, wherein the active layer is uniform and continuous.

7. A transdermal patch as claimed in claim 5, wherein the active layer is discontinuous.

8. A transdermal patch as claimed in claim 5, wherein the active layer is embedded in the adhesive matrix such that a margin of the adhesive matrix is formed around the active layer.

9. A transdermal patch made by the process of:

depositing at least one active substance on an adhesive layer of an adhesive transfer in at least one of a random discontinuous pattern and an ordered discontinuous pattern, wherein said at least one active substance comprises at least one of a powder, a liquid and a gel;

bringing a backing layer into contact with the adhesive matrix; and laminating the backing layer to the transfer adhesive tape by the application of pressure.

10. A method of manufacturing a transdermal patch comprising the steps of:

depositing at least one active substance on an adhesive layer of an adhesive transfer tape in at least one of a random discontinuous pattern and an ordered discontinuous pattern, wherein said at least one active substance comprises at least one of a powder, a liquid and a gel;

bringing a backing layer into contact with the adhesive matrix; and laminating the backing layer to the transfer adhesive tape by the application of pressure.

11. A transdermal patch made by the process of:

depositing an active substance comprising at least one of a liquid and a semi-liquid into depressions of an embossed liner;

locating an adhesive tape including an adhesive matrix and a backing layer over the embossed layer, wherein the adhesive matrix is in contact with the embossed liner; and laminating the embossed liner to the pressure sensitive adhesive tape using heat and pressure.

12. A method of manufacturing a transdermal patch comprising:

depositing an active substance comprising at least one of a liquid and a semi-liquid into depressions of an embossed liner;

locating an adhesive tape including an adhesive matrix and a backing layer over the embossed layer, wherein the adhesive matrix is in contact with the embossed liner; and laminating the embossed liner to the pressure sensitive adhesive tape heat and pressure.

13. The method of manufacturing a transdermal patch as claimed in claim 12, further comprising the step of forming the depressions in the embossed liner.

14. A transdermal patch made by the process of:

depositing an active substance comprising at least one of a liquid and a semi-liquid into depressions of an embossed backing;

locating an adhesive transfer tape including an adhesive matrix and a release liner over the embossed backing, wherein the adhesive matrix is in contact with the embossed backing; and laminating the embossed backing to the pressure sensitive adhesive transfer tape using heat and pressure.

15. A method of manufacturing a transdermal patch comprising:

depositing an active substance comprising at least one of a liquid and a semi-liquid into depressions of an embossed backing;

locating an adhesive transfer tape including an adhesive matrix and a release liner over the embossed backing, wherein the adhesive matrix is in contact with the embossed backing; and laminating the embossed backing to the pressure sensitive adhesive transfer tape using heat and pressure.

16. A transdermal patch as claimed in claim 1, wherein the ratio of the average particle size of the active substance to the thickness of the adhesive matrix is equal to or less than five.

* * * * *